US00PP35899P3

(12) United States Plant Patent
Thompson

(10) Patent No.: US PP35,899 P3
(45) Date of Patent: Jul. 2, 2024

(54) RASPBERRY PLANT NAMED 'HFG 1359'

(50) Latin Name: ***Rubus idaeus* L.**
Varietal Denomination: HFG 1359

(71) Applicant: Hortifrut North America, Inc., Estero, FL (US)

(72) Inventor: Ellen Thompson, Watsonville, CA (US)

(73) Assignee: Hortifrut Genetics Limited, Dublin (IE)

( * ) Notice: Subject to any disclaimer, the term of this patent is extended or adjusted under 35 U.S.C. 154(b) by 0 days.

(21) Appl. No.: 17/984,636

(22) Filed: Nov. 10, 2022

(65) Prior Publication Data

US 2024/0164226 P1 May 16, 2024

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./156, 203, 204
See application file for complete search history.

(56) References Cited

U.S. PATENT DOCUMENTS

PP29,369 P2 * 6/2018 Thompson ..... Plt./204

OTHER PUBLICATIONS

Integrated Annual Regport 2022. Hortifrut. https://investor.hortifrut.com/wp-content/uploads/2023/07/Hortifrut-Memoria-Integrada-2022_ingle%CC%81s-WEB.pdf. (Year: 2022).*

* cited by examiner

*Primary Examiner* — Karen M Redden
(74) *Attorney, Agent, or Firm* — King IP Law; Joshua King

(57) ABSTRACT

A new and distinct cultivar of primocane-fruiting raspberry named 'HFG 1359'. The new variety reliably provides balanced, heavy crop load on both primocanes and floricanes, with large, broad conic, firm, semi-matte, pinkish-red colored berries suited for the fresh market. Plants possess high vigor and produce high numbers of spawn.

4 Drawing Sheets

Latin name of the genus and species of the plant claimed: *Rubus idaeus* L.

Variety denomination: 'HFG 1359'.

BACKGROUND AND SUMMARY

The new primocane-fruiting raspberry cultivar designated as 'HFG 1359' is shown herein. Botanically known as *Rubus idaeus* L., the new variety 'HFG 1359' resulted from a hand-pollinated cross of female parent 'Pacific Gema' (U.S. Plant Pat. No. 28,080P3), and the male parent 'Pacific Starlet' (U.S. Plant Pat. No. 28,046P3), both of which are releases from the same program. Hand-pollination from this directed cross occurred in April 2012. Seeds from the resulting population were harvested, cleaned, germinated, and subsequently established as seedlings in spring 2013 in Watsonville, California, Santa Cruz County, USA.

'HFG 1359' was first identified in October 2013 in a substrate block where seedlings had been planted into 10 L pots the prior spring. The selection ultimately identified as 'HFG 1359' was first propagated asexually by crown division (of that original potted 'HFG 1359' plant, which became the mother-plant for subsequent 'HFG 1359' plants) in December 2013. More specifically, the crown on the original 'HFG 1359' plant was parted into basal cane pieces (approximately 15 cm long) with root attached, re-potted and placed inside of a screenhouse. The remaining roots were chilled for 4 weeks and planted inside into an onsite greenhouse to force etiolated shoots. Once rooted, individual etiolated shoots (propagules) were planted into 10-plant plot replicates. Harvest and postharvest data were collected from plots of 'HFG 1359' for two years, from 2014 through 2016.

In January 2016, additional root pieces from the original mother-plant were planted into an on-site greenhouse. Two actively growing etiolated shoots were forced from roots, transplanted and potted. Once established, these young plants were sent to Lafayette, OR, USA, where vegetative material was established in vitro for micropropagation. Tissue-cultured plantlets of 'HFG 1359' were evaluated extensively over the next several years across diverse environments for performance and genetic stability.

BRIEF SUMMARY OF THE INVENTION

The present cultivar, 'HFG 1359' offers many advantages over the existing cultivar and maternal parent, 'Pacific Gema' (U.S. Plant Pat. No. 28,080 P3). Particularly for fruit color, 'HFG 1359' is noteworthy for its pinkish-red colored berries, as compared to the dark red fruit color of 'Pacific Gema'. Fruit color of 'HFG 1359' is non-darkening under postharvest evaluations, maintaining a fresh appearance. In contrast, 'Pacific Gema' darkens substantially during postharvest holding tests. Further, berries of 'HFG 1359' detach more easily from the receptacle than 'Pacific Gema', which aids in improved harvest efficiency. The non-darkening color, and case of fruit detachment offers significant advantages to growers, who require fast picking speeds to maintain harvest efficiency.

In contrast to the male parent 'Pacific Starlet (U.S. Plant Pat. No. 28,046 P3), 'HFG 1359' is significantly greater in vigor, plant fitness, and provides greater yields. A combination of robust plant growth and consistently greater yields are critical for growers to stay competitive. Like its male parent, 'HFG 1359' develops medium-sized raspberries.

The present cultivar, 'HFG 1359' was derived from the same parental cross that resulted in 'PBBrasp1381' (U.S. Plant Pat. No. 29,369 P2). It offers reduced acidity and increased sugar content in comparison to 'PBBrasp1381'. These differences allow 'HFG 1359' to offer an improved eating experience for consumers of raspberries that prefer a sweeter perceived flavor. 'HFG 1359' is noteworthy for its pinkish-red colored berries, as compared to the darker red fruit color of 'PBBrasp1381'.

'HFG 1359' offers advantages over commercial known variety 'Finnberry' (U.S. Plant Pat. No. 35,090 P2). 'HFG 1359' is significantly firmer than 'Finnberry' which allows for a longer shelf life. Fruit color of 'HFG 1359' is non-darkening under postharvest evaluations, maintaining a fresh appearance. In contrast, 'Finnberry' darkens substantially during postharvest holding tests.

Thus, these characteristics help define 'HFG 1359' as a new and distinct cultivar of primocane-fruiting raspberry. 'HFG 1359' may be recognized by its non-darkening, pinkish-red berries that detach easily from the receptacle, and provide excellent harvesting and packing efficiency for growers.

BRIEF DESCRIPTION OF THE PHOTOGRAPHS

DETAILED DESCRIPTION

Figure 1:
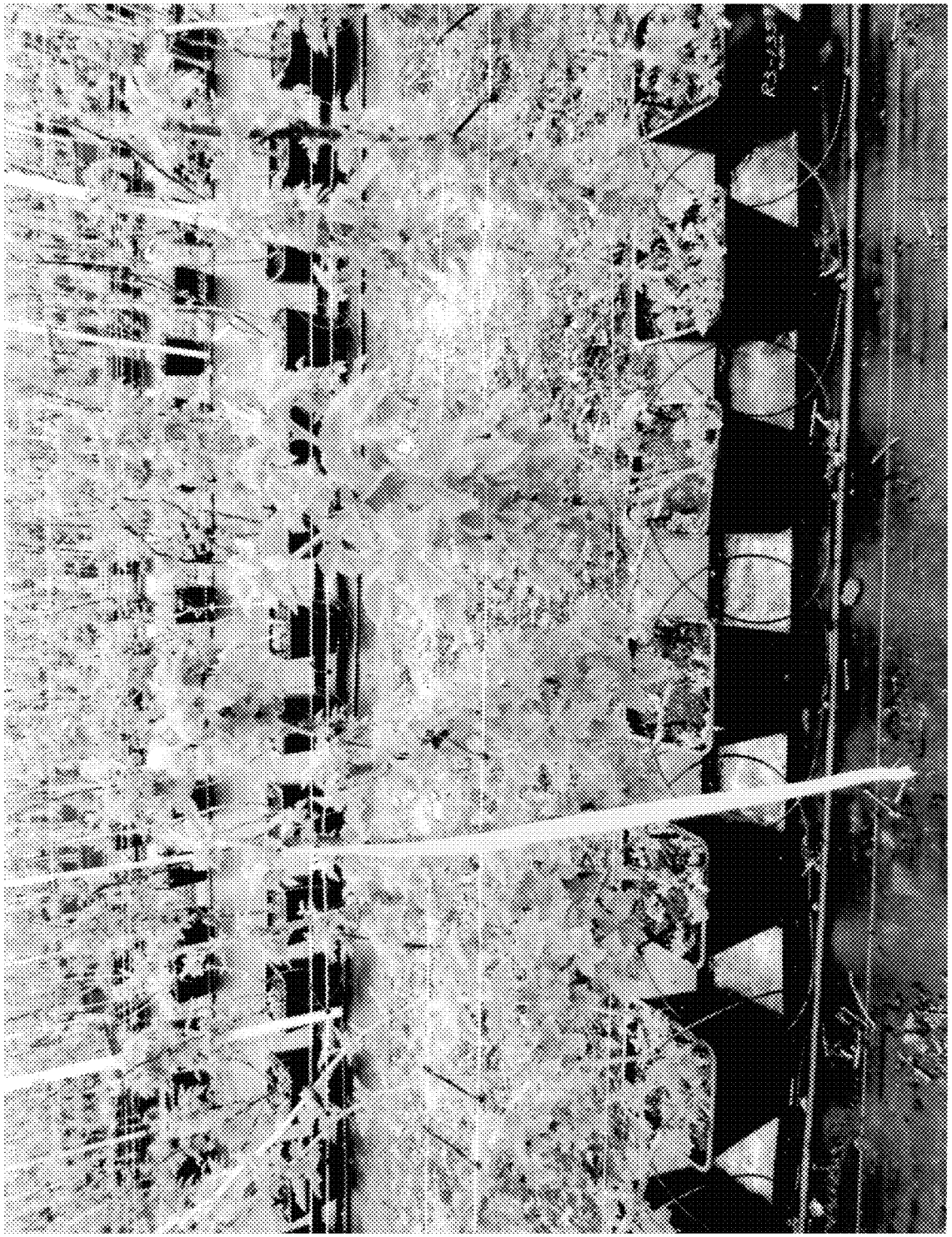
FIG. 1 is a photograph showing the uniform floricane budbreak of raspberry cultivar 'HFG 1359'.
Figure 2:
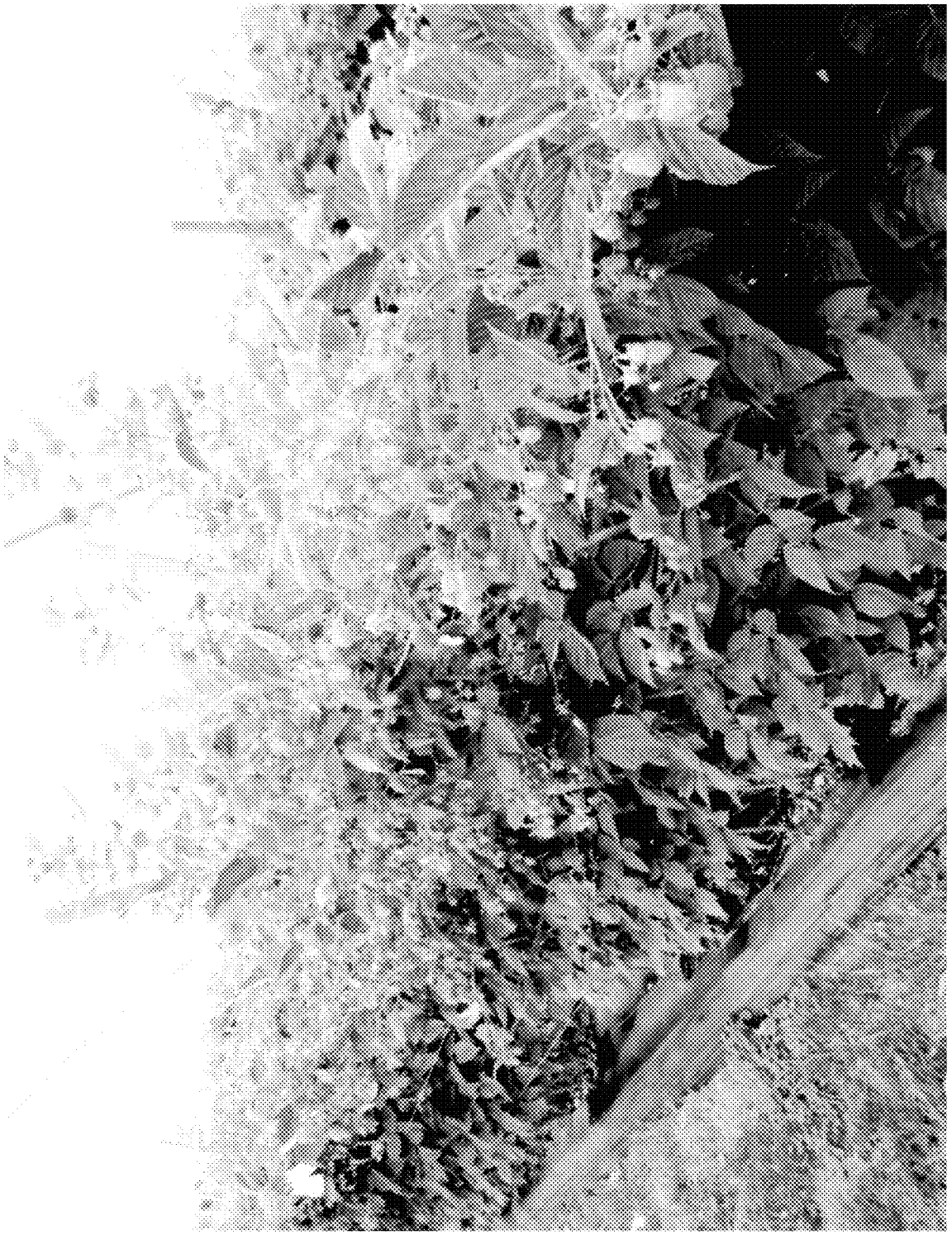
FIG. 2 is a photograph of 'HFG 1359' displaying cropload throughout its floricane canopy.
Figure 3:
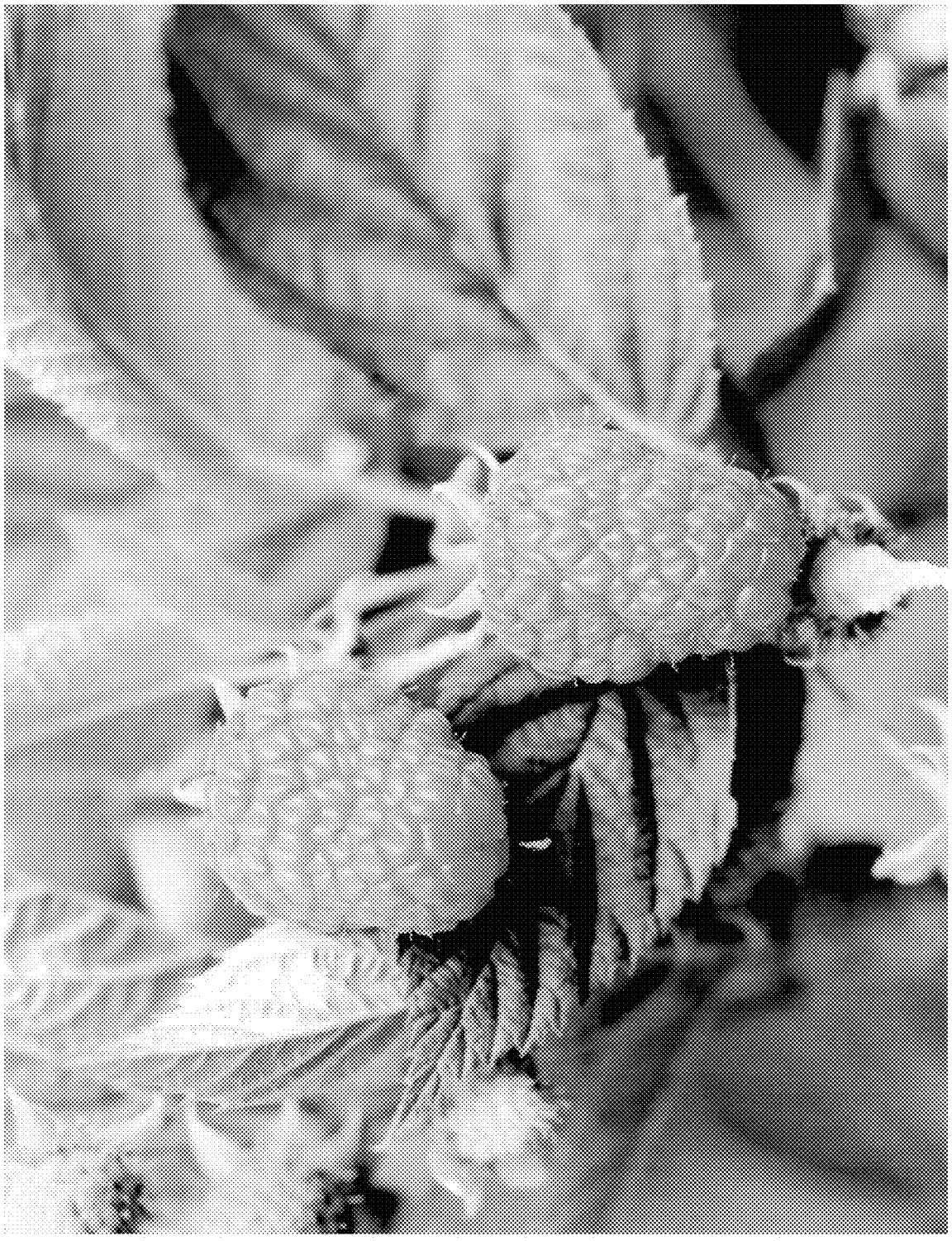
FIG. 3 is a photograph displaying the fruit shape of raspberries of cultivar 'HFG 1359' on primocanes.
Figure 4:
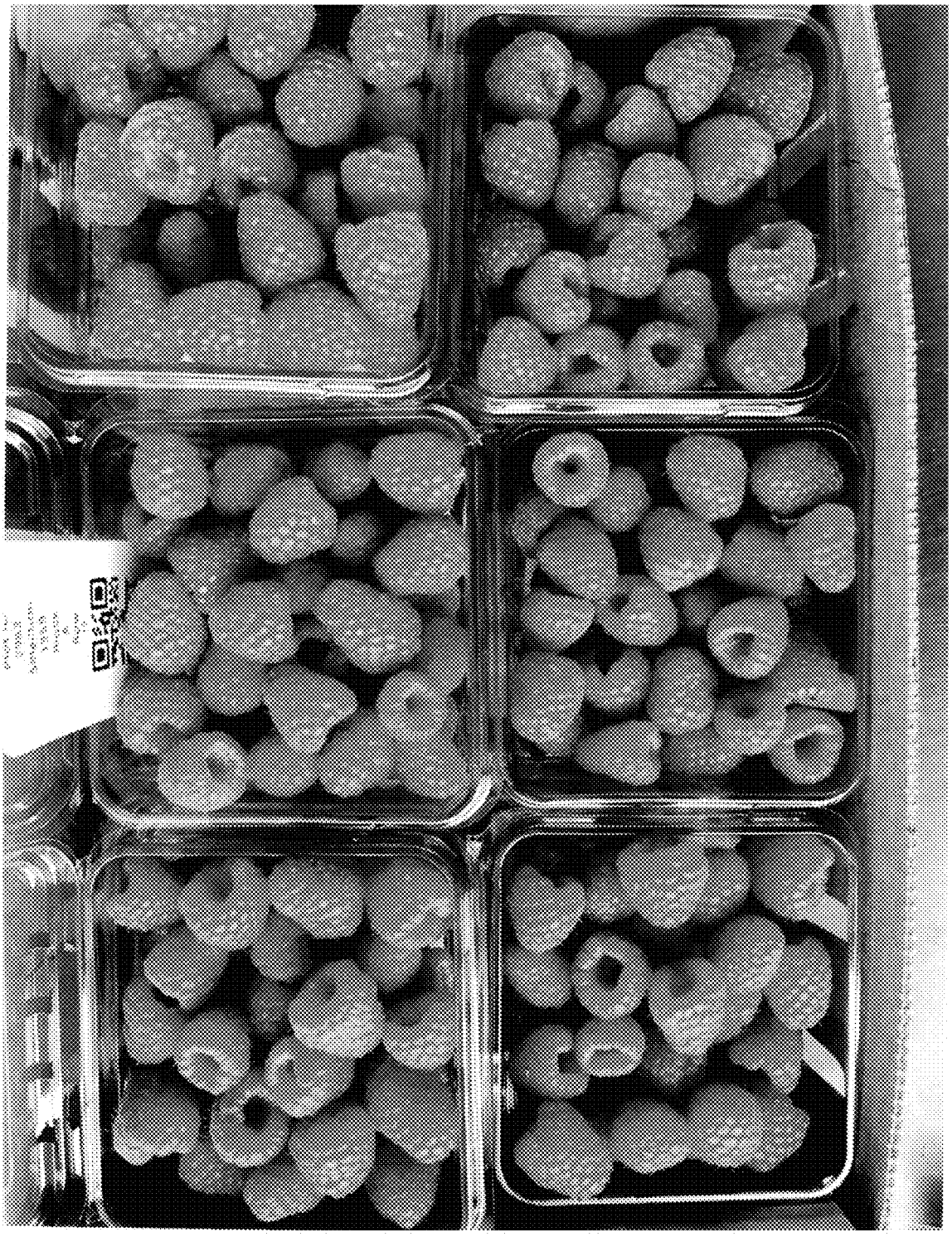
FIG. 4 is a photograph showing fruit color and uniformity of raspberries of cultivar 'HFG 1359' after harvest and placement into clamshells.

Note: statements of characteristics herein represent exemplary observations of the cultivar herein and will vary depending on time of year, location, annual weather, etc.

Cultivar Name: 'HFG 1359'

Classification:

Family: Rosaceae

Botanical name: *Rubus idaeus* L.

Common name: Raspberry

Parentage:

Female parent: 'Pacific Gema', U.S. Plant Pat. No. 28,080P3

Male parent: 'Pacific Starlet' U.S. Plant Pat. No. 28,046P3

Growing location for the observations herein: Watsonville, California, USA.

Time of year (season): May 18 through June 25, on average, for floricanes, and 7 September through 15 October, on average, for primocanes.

Age of plants used for this discussion: Crown age of about 2 years; floricane age 13 months; primocane age 8 months. Trial plants are ordered from the nursery each year for testing. Three representative specimens were chosen for USPTO botanical data collection, and data was averaged.

Age of plants used for the photographs in the Figures: Crown age of about 2 years; floricane age 13 months; primocane age 8 months.

Type of greenhouse covering or growing structure, or field: High tunnel over substrate-grown plants.

Light: Natural.

Color terminology refers to The RHS Colour Chart, Royal Horticultural Society, Fifth Edition, London, United Kingdom (2007).

Observations for floricanes herein were made in June 2022. Observations for primocanes herein were made in October 2021.

Plant:

*Form/shape.*—Vase.

*Growth habit.*—Erect.

*Height.*—236 cm, as measured from cane base to apex.

*Spread.*—0.75 cm as measured from terminal leaflet tip to terminal leaflet tip.

*Propagation methods.*—Tissue culture.

*Time to initiate and develop roots.*—24 days.

*Root description.*—Fibrous.

Primocanes:

*Cane diameter.*—Base: 1.2 cm|Middle: 1.0 cm|Tip: 0.4 cm.

*Cane length.*—2.1 m.

*Number of nodes per cane.*—41.

*Internode length.*—Base: 6.2 cm|Middle: 9.5 cm|Tip: 4.4 cm.

*Number of canes/hills.*—4 to 6.

*Cane color.*—Base — RHS 144C; Middle and tip — RHS 144A.

*Spines.*—Present.

*Spine density.*—Base: 12.0/cm$^2$|Middle: 9.3/cm$^2$|Tip: 3.3/cm$^2$.

*Spine shape.*—Acute.

*Spine length.*—0.05 cm.

*Spine width.*—0.01 cm.

*Spine apex descriptor.*—Acuminate.

*Spine color.*—RHS 181A.

*Vegetative bud shape.*—Rounded.

*Vegetative bud length.*—1.0 cm.

*Vegetative bud diameter (base).*—0.6 cm.

*Vegetative bud diameter (tip).*—0.08 cm.

*Vegetative bud color.*—RHS 143A.

Floricanes:

*Cane diameter.*—Base — 1.4 cm|Middle — 1.1 cm|Tip — 0.9 cm.

*Cane length.*—90.2 cm.

*Number of nodes per cane.*—17. Internode Length: Base — 5.7 cm|Middle — 4.9 cm|Tip — 3.4 cm.

*Cane color.*—Lower Cane — RHS 174A|Upper Cane — RHS 165A.

*Spines.*—Present. Spine density: Base: 7/cm$^2$|Middle: 4/cm$^2$|Tip: 3/cm$^2$. Spine shape: Acuminate. Spine length: 0.07 cm. Spine width: 0.01 cm. Spine apex descriptor: Acuminate. Spine color: RHS 181B.

*Reproductive bud shape.*—Rounded.

*Reproductive bud length.*—1.1 cm.

*Reproductive bud diameter (base).*—0.6 cm.

*Reproductive bud diameter (tip).*—0.08 cm.

*Reproductive bud color.*—RHS 143A.

*Reproductive bud texture.*—Pubescent.

*Winter hardiness.*—This cultivar is best adapted to the mild coastal conditions of USDA Hardiness Zone 9b (Watsonville, California). Since 2013, this cultivar has also been successfully tested under zero chill environments of central Mexico (Ciudad Guzman, Jalisco) and low-chill environments of Portugal (Odemira).

*Drought/heat tolerance.*—Pollen viability and fruit quality of raspberry generally begins to decline above 30° C. This is consistent with observations of 'HGF 1359'. Raspberries are generally not drought tolerant, and 'HFG 1359' has not been tested in unirrigated plots.

Leaves:

*Complete leaf.*—Length: 17.9 cm. Width: 21.0 cm. Number of leaflets: 3 to 5.

*Terminal leaflet.*—Size. Length: 12.8 cm. Width: 9.1 cm. Length/Width ratio: 1.7 cm. Leaf shape of apex: Acuminate. Leaf shape of base: Cordate. Leaf margin: Serrate. Leaf texture: Rigid interveinal puckering. Number of serrations per leaf: 87 serrations. Leaf shape of serrations: Flexuous — Flexuous. Leaf color: Upper Surface: RHS 137B. Lower Surface: RHS 144D. Leaf venation pattern: Palmate. Leaf venation color: Upper surface: RHS 144C. Lower surface: RHS N144D. Leaf pubescence density: Present on underside only; moderate. Color of leaf pubescence: RHS 137B. Shape of leaf in cross-section: Oval. Number of leaflets/leaf: Primocane: 3-5 Floricane: 3. Interveinal blistering within leaf: Present, mild. Leaf glossiness: Upper Surface: Matte. Lower Surface: Matte. Leaf rugosity: Medium.

Primocane leaves: Petiole length: 5.7 cm. Petiole diameter: 2.2 cm. Petiole Color: Upper: RHS 137D. Lower: RHS 144D. Rachis length: 3.4 cm. Stipule length: 0.8 cm. Stipules per leaf: 2. Stipule Width: 0.07 cm. Stipule Color: Upper Surface: RHS 137B. Lower Surface: RHS 144C.

*Terminal leaflet.*—Length: 10.2 cm. Width: 8.5 cm. Rachis length: 3.1 cm.

*Distal lateral leaflet.*—Length: 8.2 cm. Width: 3.2 cm. Petiolule length: Sessile.

*Basal lateral leaflet.*—Length: 8.1 cm. Width: 3.6 cm. Petiolule length: 0.4 cm.

*Floricane leaves.*—Petiole length: 5.1 cm. Stipule length: 0.6 cm. Stipules per leaf: 2. Stipule Width: 0.06 cm. Stipule Color: Color Upper surface: RHS 137B. Lower surface: RHS 144C.

*Terminal leaflet.*—Length: 9.8 cm. Width: 7.1 cm. Rachis length: 2.0 cm. Distal lateral leaflet: Length: 7.9 cm. Width: 5.9 cm.

*Petiolule.*—Length: 1.6 cm. Diameter: 0.1 cm. Color: Upper — RHS 138A. Lower — RHS 144A.

*Basal lateral leaflet.*—Length: 10.3 cm. Width: 5.5 cm.

Flowers:

*Time of flowering* (50% *of plants at first flower*).—Approximately 160 days after planting (on primocanes).

*Flower size.*—Length: 0.8 cm. Diameter: 0.7 cm.

*Fragrance.*—None.

*Peduncle.*—Length: 3.2 cm. Diameter: 0.2 cm. Color: RHS 143A. Pubescence: Present. Texture: Smooth, with few spines.

*Perianth.*—Flowering trusses shape: Truncate.

*Petals.*—Color: Upper — RHS 150A|Lower — RHS 150A. Number per flower: 5 petals. Shape: Obovate. Length: 0.7 cm. Width: 0.2 cm. Apex descriptor: Rounded. Base Descriptor: Cuneate. Margin descriptor: Entire. Texture: Smooth with visible striations.

*Sepals.*—Quantity: 5. Length: 0.7 cm. Width: Base — 0.4 cm|Mid— 0.3 cm|Tip — 0.1 cm. Color: RHS 145A. Apex descriptor: Acuminate. Margin descriptor: Entire. Texture: Pubescent.

*Pedicel.*—Color: RHS 143C. Length: 1.6 cm. Diameter: 0.1 cm.

Reproductive organs: Self-fertile: Yes.

*Male.*—Stamen Number: 98. Filament. Length: 0.4 cm. Diameter: 0.01 cm. Color: RHS 145B. Anther. Length: 0.01 cm. Diameter: 0.04 cm. Color: RHS 162A. Pollen. Color: RHS 162A. Amount: Heavy.

*Female.*—Style. Length: 0.3 cm. Diameter: 0.06 cm. Color: RHS 157B. Stigma. Length: 0.3 cm. Diameter: 0.08 cm. Color: RHS 157B. Ovary. Length: 0.01 cm. Diameter: 0.06 cm. Color: N144D.

Fruit:

*Predominant shape.*—Broad Conical. Weight (g): 6.7 g. Length: 2.8 cm. Width: Base — 2.2 cm|Mid — 1.7 cm|Tip — 1.3 cm. Length/Width ratio: 1.3 cm. Receptacle. Length: 1.6 cm. Diameter: Base — 0.6 cm|Mid — 0.4 cm|Tip — 0.2 cm. Color: RHS 10D. Drupelet. Length: 0.5 cm. Diameter: 0.2 cm. Number: 102. Weight: 0.04 g. Fruit Color. External: RHS 44B. Internal: RHS 46A. Firmness of skin: Firm. Firmness of flesh: Firm. Hollow center: Present. Number of fruit per node: 5-7. Time of ripening (50% of plants with first fruit): 190 days after planting, on average. Time of fruiting: Late spring to early summer on floricanes; late summer to early autumn on primocanes. Type of Bearing: Remontant. Fruit Yield: 22,647 lb./a, on average. Average Brix: 10.6. Typical market use: Fresh. Keeping quality: Excellent. Shipping quality: Excellent.

Pest and disease resistance: 'HPG 1359' shows tolerance to yellow rust (*Phragmidium rubi-thunbergii*), a common fungal disease under commercial conditions. 'HPG 1359' has exhibited mild susceptibility to *Phytophthora rubi* root rot and *Didymella.*

What is claimed is:

1. A new and distinct cultivar of Raspberry plant named 'HFG 1359' as described and shown herein.

* * * * *